United States Patent [19]

Michaelson

[11] Patent Number: 4,810,707

[45] Date of Patent: Mar. 7, 1989

[54] HERPES SIMPLEX TREATMENT

[75] Inventor: Joseph B. Michaelson, Glendale, Calif.

[73] Assignee: Meditech Pharmaceuticals, Inc., Encino, Calif.

[21] Appl. No.: 177,886

[22] Filed: Mar. 29, 1988

Related U.S. Application Data

[63] Continuation of Ser. No. 20,135, Feb. 25, 1987, abandoned, which is a continuation of Ser. No. 768,913, Aug. 22, 1985, abandoned, which is a continuation of Ser. No. 381,870, May 25, 1982, abandoned.

[51] Int. Cl.⁴ ............................................ A61K 31/435
[52] U.S. Cl. .................................................. 514/277
[58] Field of Search ........................................ 514/277

[56] References Cited

U.S. PATENT DOCUMENTS

| | | | |
|---|---|---|---|
| 2,764,590 | 9/1956 | Kottler et al. | 546/342 |
| 2,827,465 | 3/1958 | Buzas et al. | 546/342 |
| 3,526,635 | 9/1970 | Halpern et al. | 546/343 |
| 4,243,678 | 1/1981 | Krastinat | 424/319 |
| 4,250,183 | 2/1981 | Krastinat | 424/263 |
| 4,256,763 | 3/1981 | McHugh | 424/285 |

OTHER PUBLICATIONS

Chem. Abstracts 92:47265e (1979).
Chem. Abstracts 88:58208g (1977).

*Primary Examiner*—Albert T. Meyers
*Assistant Examiner*—John M. Kilcoyne
*Attorney, Agent, or Firm*—Christie, Parker & Hale

[57] ABSTRACT

Method for the effective management of Herpes Simplex including the administration of an effective dosage of phenol, 4,4'-(2-pyridinyl methylene) bis diacetate (ester), in combination with a carrier, vitamins, or other therapeutic agents, and an effective dosage product comprising phenol, 4,4'-(2-pyridinyl methylene) bis,-diacetate (ester) for carrying out the method.

5 Claims, No Drawings

HERPES SIMPLEX TREATMENT

CROSS-REFERENCE TO RELATED APPLICATIONS

This is a continuation of application Ser. No. 020,135, filed Feb. 25, 1987, which is a continuation of application Ser. No. 768,913, filed Aug. 22, 1985, which is a continuation of application Ser. No. 381,870, filed May 25, 1982, all abandoned.

TECHNICAL FIELD

This invention relates to treatment of Herpes Simplex (*Herpesvirus hominis*), a viral disease of widespread occurrence. Herpes Simplex occurs in two antigenic types, *Herpes febrilis* and *Herpes genitalis*, referred as Type 1 and Type 2. Infection is usually manifested by the appearance of vesicular eruptions, oral herpetic lesions, commonly referred to as fever blisters, or cold sores about the lips in the instance of Herpes Simplex Type 1, and vesicular lesions on and about the male or female genitalia in the instance of Herpes Simplex Type 2. Persons with Herpes Simplex infections are likely to have recurrent periods of lesion development spaced by periods of remission. Management of the condition involves easing the itching sensation which accompanies the lesion periods, and speeding remission.

BACKGROUND ART

While no cure is presently known for Herpes Simplex in either form, certain substances have been advanced for management of the disease. In U.S. Pat. No. 4,256,763 to McHugh a method of treating inflammatory viral infections such as Herpes Simplex and acne was disclosed involving the application of 3,3-bis (p-hydroxyphenyl) phthalide, in amounts up to 100 milligrams, preferably 15 to 30 milligrams initially and repetitively at predetermined intervals. Because 3,3-bis (p-hydroxyphenyl) phthalide is a cathartic, there is an unpleasant side effect to its use which suggests reduced usage concentrations, but the patentee does not suggest any lower dosage will be effective in Herplex Simplex management.

SUMMARY OF THE INVENTION

It is an object of the present invention to provide an effective Herpes Simplex treatment at much reduced dosage levels to minimize side effects. It is another object to provide a new use for phenol, 4,4'-(2-pyridinyl methylene) bis diacetate (ester). It is a further object to provide for the rapid amelioration of Herpes Simplex symptoms, itching, lesion development and the like, by treatment with quite low quantities of phenol, 4,4'-(2-pyridinyl methylene) bis diacetate (ester), and to maintain the patient in a remissive state with continued low dosage treatment after remission. Still other objects include provision of products comprising phenol, 4,4'-(2-pyridinyl methylene) bis diacetate (ester), carriers and therapeutic agents for coapplication with phenol, 4,4'-(2-pyridinyl methylene) bis diacetate (ester).

These and other objects of the invention to become apparent hereinafter, are realized in accordance with the invention in the method of treatment of Herpes Simplex infection condition which includes administering an effective dosage of phenol, 4,4'-(2-pyridinyl methylene) bis,- diacetate (ester) to a person having an Herpes Simplex condition.

In particular embodiments, the method includes administering such dosage orally, administering a dosage of from about 0.1 to about 9.5 milligrams of phenol, 4,4'-(2-pyridinyl methylene) bis diacetate (ester), suspending the phenol, 4,4'-(2-pyridinyl methylene) bis,- diacetate (ester) in a carrier for administration, combining the phenol, 4,4'-(2-pyridinyl methylene) bis,- diacetate (ester) with a second therapeutic agent in an effective dosage for administration therewith, e.g. by selecting an effective dosage of one or more vitamins for coadministration with the phenol, 4,4'-(2-pyridinyl methylene) bis diacetate (ester), and carrier if any, and maintaining the phenol, 4,4'-(2-pyridinyl methylene) bis,- diacetate (ester) free of enteric coating for administration.

The invention further contemplates provision of a product comprising a dosage of phenol, 4,4'-(2-pyridinyl methylene) bis,- diacetate (ester) effective upon oral ingestion for management of Herpes Simplex, and less than is effective for cartharsis of the person receiving the dosage and combined with an ingestible carrier. Typically, the product comprises a dosage between 0.1 and 9.5 milligrams, and may further comprise one or more vitamins in effective dosage, preferably free of an enteric coating.

PREFERRED MODES phenol, 4,4'-(2-pyridinyl methylene) bis diacetate (ester), commonly referred to as Bisacodyl, is a diphenyl trimethane suitably prepared from 2-pyridinecarboxaldehyde condensed with phenol in the presence of sulfuric acid or other dehydrant, followed by esterification with acetic anhydride and anhydrous sodium acetaate, as described in U.S. Pat. No. 2,764,590. It is a white to off-white crystalline powder slightly soluble in water but fairly soluble in common organic solvents. It is known to be used as a contact laxative, acting to increase peristalsis throughout the large intestine. A typical dose as a laxative is oral or rectal not less than 10 milligrams and up to 30 milligrams and is administered in an enteric coating to ensure passage to the large intestine. It is known to inhibit glucose absorption and intestinal Na-K-ATPase activity.

The effectiveness of phenol, 4,4'-(2-pyridinyl methylene) bis,- diacetate (ester) in treatment of Herpes Simplex is not to be expected from a study of its past usages or chemical structure, and is not scientifically explainable at this time. It has been found surprisingly effective in Herpes Simplex management, causing nearly immediate remission and suppressing recurrence, although administered at quite moderate levels, less than those recommended for laxative action, and far less than 3,3-bis (p-hydroxyphenyl) phthalide dosages recommended in U.S. Pat. No. 4,256,763. The use of phenol, 4,4'-(2-pyridinyl methylene) bis,- diacetate (ester) as taught herein thus enables Herpes Simplex management with reduced incidence of side effects than encountered with the use of alternative methodologies.

The phenol, 4,4'-(2-pyridinyl methylene) bis,- diacetate (ester) may be combined with other therapeutic agents each for its own purpose e.g. to relieve stress, or to enhance the effectiveness of the phenol, 4,4'-(2-pyridinyl methylene) bis,- diacetate (ester) when administered. Such agents as vitamins A, D, E, C, Folic acid, B-1, B-2, Niacin, B-6, and B-12, among others can be combined with the phenol, 4,4'-(2-pyridinyl methylene) bis diacetate (ester). Other agents for combining with phenol, 4,4'-(2-pyridinyl methylene) bis diacetate (ester)

include amino acids, such as lysine and leucine; proteins such as gelatin and gliadin; or carbohydrates, e.g starch, lactose and the like.

Whether administered orally, topically or intravenously, the phenol, 4,4'-(2-pyridinyl methylene) bis,-diacetate (ester) may be suitably dispersed in a carrier, e.g. tablet or capsule carriers and components such as excipients, bulking agents, lubricants, disintegrants, dyes and the like as are known in tablet making technology for the purpose of easing the administration of the phenol, 4,4'-(2-pyridinyl methylene) bis diacetate (ester). The term carrier further embraces vehicles used or useful in preparing injection form of the phenol, 4,4'-(2-pyridinyl methylene) bis,- diacetate (ester) products of the invention, such as sesame oil and the like.

EXAMPLE I

Capsules of phenol, 4,4'-(2-pyridinyl methylene) bis,-diacetate (ester) were prepared by mixing per capsule 3.35 milligrams of phenol, 4,4'-(2-pyridinyl methylene) bis,- diacetate (ester) with 490 milligrams of an aliquot of a mixture of vitamins comprising:
Vitamin A: 2500 units
Vitamin D: 400 units
Vitamin E: 15 units
Vitamin C: 60 mg.
Folic acid: 0.3 mg.
Vitamin B-1: 1.0 mg.
Vitamin B-2: 1.2 mg.
Niacin: 13.5 mg.
Vitamin B-6: 1.0 mg.
Vitamin B-12: 4.5 mg.
blended with 2 parts of cornstarch per part of vitamin mix.

Adult males having a virulent recurrence of Herpes Simplex Types 1 and 2 were given a series of EXAMPLE I capsules prepared as above, or a like CONTROL I capsule prepared with phenolphthalein (3,3-bis (p-hydroxyphenyl phthalide) rather than phenol, 4,4'-(2-pyridinyl methylene) bis diacetate (ester), or a CONTROL II as taught in U.S. Pat. No. 4,256,763. The CONTROL II capsules comprised:
Phenolphthalein: 30 mg.
Acetominophen: 325 mg.
Chlorpheniramine Maleate: 2 mg.
Caffein: 33 mg.
Phenylephrine HCL: 10 mg.

The effective dosage rate for the CONTROL I and II treatments was 30 milligrams per 8 hours for the first day, and a like amount at 12 hour intervals thereafter. The EXAMPLE I dosage rate was one capsule (3.35 mg. per dosage) every six to eight hours on the first day and thereafter at 8 to 12 hour intervals.

All subjects showed rapid remission. The EXAMPLE I material was no less effective for being at the reduced dosage rate, and incidenceof diarrhea from the laxative effect was less of a problem than with the CONTROL I and II tests.

The inclusion of vitamins in the EXAMPLE I formulation adds stress relief factors to the formulation to ameliorate the stress which often accompanies onset of a Herpes condition.

EXAMPLE II

A second capsule formula of the invention composition was prepared from:
phenol, 4,4'-(2-pyridinyl methylene) bis diacetate (ester): 3.5 mg.
phenactin: 350. mg.
chloropheniramine maleate: 3. mg.
caffein: 38. mg.
phenylpropanolamine HCL: 9. mg.
by blending the ingredients eutectically.

EXAMPLE III

A tablet form of the invention dosage is prepared by blending phenol, 4,4'-(2-pyridinyl methylene) bis diacetate (ester), 3.5 mg., 100 mg. lactose, 100 mg. starch, and 10 mg. talc as a lubricant. It will be noted that this formulation can be packaged in capsule form with the omission of the talc and adjusting the lactose and starch concentration accordingly.

EXAMPLE IV

A protein containing capsule is prepared by blending eutectically phenol, 4,4'-(2-pyridinyl methylene) bis diacetate (ester), 3.5 mg., 200 mg. lactose, 100 mg. gliadin or gelatin protein, and about 100 mg. of the amino acid lysine.

EXAMPLE V

An intramuscular injectable formulation is prepared by by blending, per dosage, 5 cc. sesame oil, 250 units of Vitamin E, and 5 mg. of phenol, 4,4'-(2-pyridinyl methylene) bis diacetate (ester).

I claim:

1. A method for treating Herpes Simplx infection condition which includes administering an effective dosage of phenol, 4,4'-(2-pyridinyl methylene) bis,- diacetate (ester) for treating Herpes Simplex infection to a person having said condition.

2. The method according to claim 1, wherein said effective dosage is administered orally.

3. The method according to claim 1 or 2, wherein said effective dosage is from about 0.1 to about 9.5 milligrams of phenol, 4,4'-(2-pyridinyl methylene) bis, -diacetate (ester).

4. The method according to claim 1 wherein said phenol, 4,4'-(2-pyridinyl methylene) bis,-diacetate (ester) is suspended in a pharmaceutically acceptable carrier for administration.

5. The method according to claim 1, wherein said phenol, 4,4'-(2-pyridinyl methylene) bis,- diacetate (ester) is maintained free of an enteric coating for administration.

* * * * *

UNITED STATES PATENT AND TRADEMARK OFFICE
CERTIFICATE OF CORRECTION

PATENT NO. : 4,810,707

DATED : March 7, 1989

INVENTOR(S) : Joseph B. Michaelson

It is certified that error appears in the above-identified patent and that said Letters Patent is hereby corrected as shown below:

Column 1, line 43, "Herplex" should read "Herpes"; column 2, line 20, "cartharsis" should read "catharsis"; column 2, line 34, "acetaate" should read "acetate"; column 4, line 35, delete the second "by"; column 4, line 39, "Simplx" should read "Simplex."

Signed and Sealed this

Twenty-fourth Day of April, 1990

Attest:

HARRY F. MANBECK, JR.

Attesting Officer     Commissioner of Patents and Trademarks